United States Patent [19]

Chamberlin, Sr.

[11] Plant 5,103

[45] Sep. 13, 1983

[54] PEACH TREE

[75] Inventor: Thomas O. Chamberlin, Sr., Visalia, Calif.

[73] Assignee: H. P. Metzler & Sons, Inc., Del Rey, Calif.

[21] Appl. No.: 323,982

[22] Filed: Nov. 23, 1981

[51] Int. Cl.[3] ..... A01H 5/00
[52] U.S. Cl. ..... Plt./43
[58] Field of Search ..... Plt./43

[56] References Cited

U.S. PATENT DOCUMENTS

P.P. 3,583 8/1974 Merrill ..... Plt./43
P.P. 4,508 3/1980 Zaiger ..... Plt./43

*Primary Examiner*—James R. Feyrer
*Attorney, Agent, or Firm*—Huebner & Worrel

[57] ABSTRACT

A peach tree, denominated "Ryans Sun," producing freestone fruit having a dark red color with bright yellow flesh of very firm and crisp character and a skin which is tenacious to the flesh ripening in the last week of August.

1 Drawing Figure

BACKGROUND OF THE VARIETY

The present invention relates to a new and distinct variety of peach tree, denominated "Ryans Sun," broadly characterized by its full freestone fruit having a dark red color with bright yellow flesh and more particularly to such a peach tree wherein the fruit has very firm and crisp flesh with a skin which is tenacious to the flesh and which ripens for picking in the last week of August after the patented O'Henry peach in the San Joaquin Valley of California.

The commercial market for fresh fruit is dependent to a large degree upon varieties which produce fruit possessing those characteristics allowing the fruit to withstand the rigors of picking, packing and shipping without appreciable damage in appearance or quality. Since such fruit must frequently be shipped great distances under conditions such as to cause substantial deterioration in fruit of the less hardy varieties, a major share of the commercial market is composed of the more durable varieties. The commercial value of such fruit is enhanced where it is of high color and reaches maturity late in the season. The O'Henry peach tree (U.S. Plant Pat. No. 2,964) has good qualities in many of these respects. The variety of the present invention produces fruit of very good shipping quality in that its flesh is very firm and crisp with a skin which is tenacious to the flesh thereby resisting damage in handling and shipping. The fruit is further characterized by its deep red color which provides an attractive and appealing appearance enhancing its commercial value. The fruit is still further characterized by its ripening time which is after the O'Henry peach. Thus, the fruit of the instant variety possesses many of the best commercial attributes of the O'Henry peach, but is distinct therefrom, among other respects in ripening after the O'Henry peach.

ORIGIN AND ASEXUAL REPRODUCTION OF THE NEW VARIETY

The instant new variety of peach tree was discovered by myself in 1976 and is a newly found seedling of the patented O'Henry peach tree. Seeds of the O'Henry peach tree were planted in a plot in the nursery of H. P. Metzler & Sons, Inc. at 5286 South Del Rey Avenue, Del Rey, Calif. 93616 in 1973 and 1974. The first fruit of the present variety was observed in 1976 and its distinctive characteristics discovered at that time. The present variety was asexually propagated under my direction at H. P. Metzler & Sons, Inc. in 1978 by collecting buds of the newly found seedling and budding a number of trees with these buds. In 1979, trees of this new variety were planted in a test block on Ranch No. 18 of H. P. Metzler & Sons, Inc. at Del Rey, Calif. Trees of the new variety were observed in the test block over several growing seasons and the fruit and tree characteristics resulting from such asexual reproduction proved to be identical to those of the original seedling of the new variety.

SUMMARY OF THE NEW VARIETY

The instant variety of peach tree is characterized by its full freestone fruit having a dark red color with bright yellow flesh of a very firm and crisp character and skin which is tenacious to the flesh, a tight pit cavity bounded by flesh of red coloration and ripening in the last week of August.

BRIEF DESCRIPTION OF THE DRAWING

The accompanying drawing is a color photograph of five mature fruit of the instant variety, one positioned to show the side, a second positioned to show the stem, a third positioned to show the apex, a fourth sliced along the suture plane with the pit left in place and a fifth sliced along the suture plane with the pit removed to expose the pit cavity. A representative twig is also shown in the photograph with characteristic leaves.

DETAILED DESCRIPTION

Referring more specifically to the pomological details of this new and distinct variety of peach tree, the following characteristics were observed under the ecological conditions prevailing at the nursery of H. P. Metzler & Sons, Inc. at Del Rey, Fresno County, Calif. and is an outlined description thereof. All major color code plate identifications are by reference to the Color Name Chart of the Inter-Society Color Council, National Bureau of Standards.

TREE

Size: Normal.

Figure: Normal, subject to pruning.
Productivity: Good.
Regularity of bearing: Bearing is good every year.
Trunk: Normal diameter in relation to length. Normal surface with about 20 lenticels per square inch. Color, 56 deep brown.
Branches: Normal in size and character of the surface. Color, 56 deep brown. Lenticels of medium size and about 20 per square inch.
Leaves: Normal size.
*Length.*—About 6½ inches [16.51 cm].
*Width.*—About 1¼ inches [3.175 cm] to about 1¾ inches [4.445 cm].
*Shape.*—Lanceolate.
*Color.*—Upper side (126-d-OlG) and under side (127-gy-OlG).
*Margin.*—Serrate.
*Petiole.*—About ⅜ inch [0.9525 cm] in length and about 3/32 inch [0.238125 cm] thick.
*Glands.*—Reniform and of very small size, with two opposed at base of leaf; color, 106-1-Ol.
Flower buds: Elongated and large and fluffy before opening with color starting to show at tip. Color before opening, 4-1- pink.
*Diameter.*—⅜ inch [0.9525 cm].
*Length.*—13/16 inch [2.06375 cm].
Flowers:
*Date of bloom.*—About March 10, or six to eight days after Springcrest.
*Size.*—Very large, each petal ¾ inch [1.905 cm] in length when open and 13/16 inch [2.06375 cm] in width.
*Color.*—Very large, very light pink petals, almost round and almost white 7-P-pink.
*Number of pistils and stamen.*—One pistil and about thirty-eight stamen.

FRUIT

Maturity: Reached in the San Joaquin Valley of California about August 24th to August 27th.
Size: Good uniformity having a diameter of 2¾ inches [6.985 cm] to 3½ inches [8.89 cm]. Transverse dimension in suture plane about 3 inches [7.62 cm]. Transverse dimension at right angles to suture plane about 3 inches [7.62 cm].
Form:
*Uniformity.*—Good.
*Shape.*—Symmetrical.
Suture.—Very smooth and shallow extending from the base to the apex about 4 inches [10.16 cm] to about 4½ inches [11.43 cm].
*Ventril surface.*—Rounded to slightly flat.
*Stem cavity.*—Rounded and about ⅝ inch [1.5875 cm] deep.
*Apex.*—Round to slightly flat.
*Base.*—Wide and flat.
*Pistol point.*—Rounded and sometimes slightly depressed.
Stem:
*Size.*—Length 5/16 inch [0.79375 cm] and Caliper 3/16 inch [0.635 cm].
Skin:
*Thickness.*—Less than 1/64 inch [0.0396875 cm].
*Texture.*—Smooth, tough and tenacious to flesh.
*Tendency to crack.*—None.
*Color.*—Very dark red (14-V deep red) to soft red (3 deep pink) with very little yellow (83 Brill y).
*Pubescense.*—Light.
Flesh:
*Color.*—(82-V.y).
*Surface of pit cavity.*—Rough.
*Color of pit cavity.*—(13 deep red).
*Amygdalin.*—Lacking.
*Juice.*—Good, no acid taste.
*Flavor.*—Good, crisp.
*Aroma.*—Good.
*Texture.*—Smooth and crisp.
*Fibers.*—None.
*Ripening.*—Even.
*Eating quality.*—Good flavor, crisp.
Stone:
*Type.*—Freestone.
*Fibers.*—None.
*Size.*—1½ inches [3.81 cm] in length and 1⅛ inches [2.8575 cm] in width. Thickness, ¾ inch [1.905 cm].
*Form.*—Normal peach pit almost round in appearance, but slightly longer than wide. Ridges running lengthwise, but curving crosswise at tip.
*Base.*—Flat and about 5/16 inch [0.79375 cm] in diameter.
*Sides.*—Very rough.
*Ridges.*—Heavy and about 1/6 inch [0.15875 cm] to ⅛ inch [0.3175 cm] in height.
*Color.*—59 — d. Br.
*Splitting tendency.*—None.
Use:
*Fresh fruit.*—Shipping.
*Keeping quality.*—Good. Fruit has been kept in storage three to four weeks without noticeable deterioration.
*Shipping quality.*—Shipping quality should be very good due to crisp nature of flesh and tenacious skin.

Although the new variety of peach tree possesses the described characteristics as a result of the growing conditions in Fresno County, Calif., in the Central portion of the San Joaquin Valley, it is to be understood that variations of the usual magnitude and characteristics incident to growing conditions, fertilization, pruning, pest control and other horticultural practices are to be expected.

Having thus described and illustrated my new variety of peach tree, what is claimed as new and desired to be secured by Letters Patent is:

1. A new and distinct variety of peach tree substantially as illustrated and described and which is characterized by its freestone fruit having a dark red color with bright yellow flesh of very firm and crisp character with a skin which is tenacious to the flesh and which ripens for picking in the last week of August and after the patented O'Henry peach.

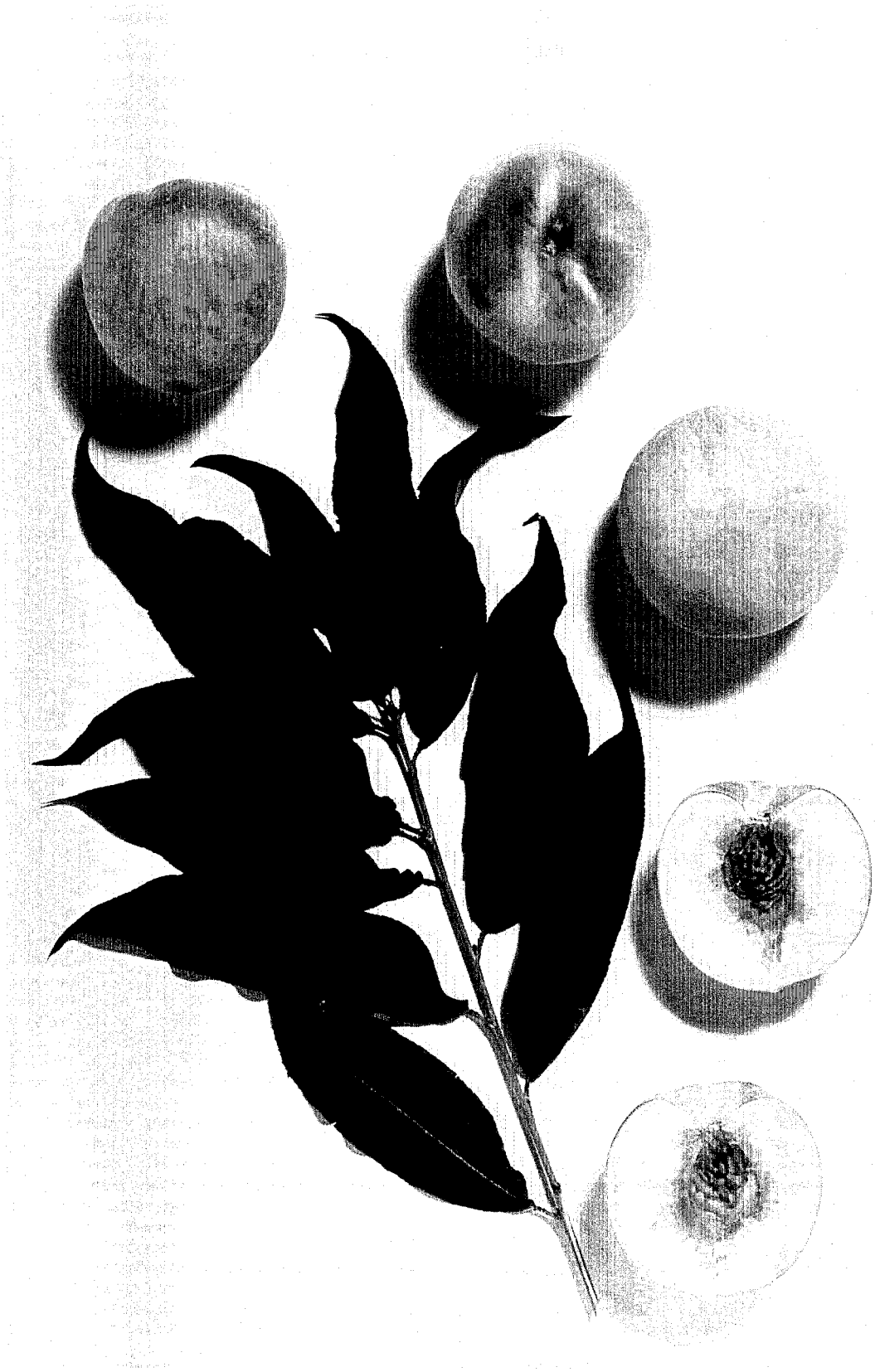

* * * * *